United States Patent
Kim et al.

(10) Patent No.: US 10,159,756 B2
(45) Date of Patent: Dec. 25, 2018

(54) COMPLEX OF MANNOSYL SERUM ALBUMIN, METHOD OF PREPARING THE SAME, OPTICAL IMAGING PROBE AND KIT COMPRISING THE SAME

(71) Applicants: Korea University Research and Business Foundation, Seoul (KR); SNU R&DB Foundation, Seoul (KR)

(72) Inventors: Hyun Koo Kim, Seoul (KR); Jae Min Jeong, Seoul (KR); Yun-Sang Lee, Seoul (KR)

(73) Assignees: KOREA UNIVERSITY RESEARCH AND BUSINESS FOUNDATION, Seoul (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/561,153

(22) Filed: Dec. 4, 2014

(65) Prior Publication Data
US 2016/0045621 A1    Feb. 18, 2016

(30) Foreign Application Priority Data
Aug. 13, 2014 (KR) .................... 10-2014-0105448

(51) Int. Cl.
*A61K 49/00* (2006.01)
*A61K 51/08* (2006.01)
*A61K 51/04* (2006.01)

(52) U.S. Cl.
CPC ...... *A61K 49/0056* (2013.01); *A61K 49/0034* (2013.01); *A61K 51/0491* (2013.01); *A61K 51/081* (2013.01); *A61K 51/088* (2013.01)

(58) Field of Classification Search
None
See application file for complete search history.

(56) References Cited

U.S. PATENT DOCUMENTS

2011/0286920 A1* 11/2011 Jeong ................ A61K 51/0482
424/1.69

FOREIGN PATENT DOCUMENTS

WO    WO 0074727 A2 * 12/2000    ......... A61K 49/0002

OTHER PUBLICATIONS

Kim et al. Intra-operative sentinel lymph node identification using a novel receptor-binding agent (technetium-99m neomannosyl human serum albumin, 99mTc-MSA) in stage I non-small cell lung cancer. 2010 Eur. J. Cardiothorac. Surg. 37: 1450-1456.*
Ohnishi et al. Organic alternatives to quantum dots for intraoperative near-infrared fluorescent sentinel lymph node mapping. 2005 Mol. Imaging 4: 172-181.*
Takagi et al. 99mTc-labeled mannosyl-neoglycoalbumin for sentinel lymph node identification. 2004 Nucl. Med. Biol. 31: 893-900.*
Jeong et al. Development of 99mTc-neomannosyl human serum albumin (99mTc-MSA) as a novel receptor binding agent for sentinel lymph node imaging. 2004 Nucl. Med. Commun. 25: 1211-1217.*
Mieog et al. Toward optimization of imaging system and lymphatic tracer for near-infrared fluorescent sentinel lymph node mapping in breast cancer. 2011 Ann. Surg. Oncol. 18: 2483-2491.*
Polom et al. Breast cancer sentinel lymph node mapping using near infrared guided indocyanine green and indocyanine green—human serum albumin in comparison with gamma emitting radioactive colloid tracer. 2012 Eur. J. Surg. Oncol. 38: 137-142.*
Kim et al. Efficient site-specific labeling of proteins via cysteines. 2008 Bioconjug. Chem. 19: 786-791. (Year: 2008).*
Altinoglu, E., et al., "Near-Infrared Emitting Fluorophore-Doped Calcium Phosphate Nanoparticles for In Vivo Imaging of Human Breast Cancer", "ACS Nano", Sep. 19, 2008, pp. 2075-2084, vol. 2, No. 10.
Kirchherr, A., et al., "Stabilization of Indocyanine Green by Encapsulation within Micellar Systems", "Molecular Pharmaceutics", Feb. 19, 2009, pp. 480-491, vol. 6, No. 2.
Mariani, G., et al., "Radioguided Sentinel Lymph Node Biopsy in Breast Cancer Surgery", "The Journal of Nuclear Medicine", Aug. 2001, pp. 1198-1215, vol. 42, No. 8.
Oh, Y., et al., "Thoracoscopic Color and Fluorescence Imaging System for Sentinel Lymph Node Mapping in Porcine Lung Using Indocyanine Green-Neomannosyl Human Serum Albumin: Intraoperative Image-Guided Sentinel Nodes Navigation", "Annals of Surgical Oncology", Dec. 6, 2013, pp. 1182-1188, vol. 21.
Rodriguez, V., et al., "Encapsulation and stabilization of indocyanine green within poly(styrene-alt-maleic anhydride) block-poly(styrene) micelles for near-infrared imaging", "Journal of Biomedical Optics", Jan./Feb. 2008, pp. 014025-1-014025-10, vol. 13, No. 1.

* cited by examiner

*Primary Examiner* — Michael G. Hartley
*Assistant Examiner* — Jennifer Lamberski
(74) *Attorney, Agent, or Firm* — Hultquist, PLLC; Steven L. Hultquist

(57) ABSTRACT

The present invention relates to a complex prepared by conjugating indocyanine green to mannosyl serum albumin in order to overcome shortcomings such as low light stability and low in vivo stability of indocyanine green that is a fluorescent dye reagent that is used during surgical operations, a preparation method thereof, an optical imaging probe comprising the same, and a kit comprising the probe.

3 Claims, 13 Drawing Sheets
(12 of 13 Drawing Sheet(s) Filed in Color)

COMPLEX OF MANNOSYL SERUM ALBUMIN, METHOD OF PREPARING THE SAME, OPTICAL IMAGING PROBE AND KIT COMPRISING THE SAME

TECHNICAL FIELD

The present invention relates to a complex prepared by conjugating indocyanine green to mannosyl serum albumin in order to overcome shortcomings such as low light stability and low in vivo stability of indocyanine green that is a fluorescent dye reagent that is used during surgical operations, a preparation method thereof, an optical imaging probe comprising the same, and a kit comprising the probe.

BACKGROUND ART

Indocyanine green (ICG), a near-infrared (NIR) fluorescent dye, is a substance approved by the US Food and Drug Administration (FDA) for use in the examination of the lymphatic system, the heart, the liver and the vascular system. Particularly, indocyanine green is known as an excellent probe for imaging of metastatic lymph nodes and mapping of sentinel lymph nodes, which are performed for early diagnosis of breast cancer.

A sentinel lymph node is the first lymph node which is closest to a primary tumor and to which cancer cells metastasize from the primary tumor. Thus, the sentinel lymph node is known as a good index that indicates the metastasis of solid tumors to local lymph nodes. If there is no metastasis of cancer cells to the sentinel lymph node, it can be seen that there is no metastasis of cancer cells to other lymph nodes, suggesting that unnecessary dissection of lymph nodes is avoided. In other words, the biopsy of a sentinel lymph node in melanoma or breast cancer makes it possible to avoid unnecessary dissection of lymph nodes.

Indocyanine green has shortcomings of low hydrophilicity, low light stability, low photon yield, and low sensitivity. Further, indocyanine green has shortcomings in that it susceptible to nonspecific aggregation and is chemically degraded by external light, solvents and a change in temperature. In addition, it has a problem in that it is easily absorbed by serum proteins due to its low molecular weight and hydrophobic nature, and is eliminated through the kidneys. The blood half-life of indocyanine green is about 2-4 minutes. Thus, the development of an indocyanine green-based probe having a long blood half-life is required to increase the efficiency of diagnosis.

Furthermore, because indocyanine green easily diffuses in vivo, there are shortcomings in that a surgical operation for dissecting a sentinel lymph node using indocyanine green imaging should be performed within 30 minutes and in that a deep lymph node cannot be detected. In an attempt to overcome such shortcomings, nanomaterial-based indocyanine green probes, for example, nanoparticles, liposomes, micelles and the like, have been studied, and there have been studies focused on increasing the in vivo and in vitro stability of indocyanine green by encapsulating indocyanine green in nanoparticles or by using micelles composed of polymers, phospholipids and calcium phosphate (A. K Kirchherr et al. Mol Pharm. 6:480, 2009, V. B. Rodriguez et al. J Biomed Opt. 13:14, 2008: E. I. Altinoglu et al. Nano. 2:2075, 2008). When indocyanine green was encapsulated in nanoparticles, the physical and chemical stability of indocyanine green against external light and temperature were significantly increased, but when an indocyanine green probe was applied for clinical diagnosis, it was not specific for the site to be imaged.

Another typical probe for lymph node imaging is a lymph node imaging probe prepared by conjugating a radioisotope to mannosyl serum albumin, which is crucially used in the imaging and diagnosis of lymph nodes in the nuclear medicine field (G. Mariani, et al. J. Nucl. Med., 42:2001). Particularly, when radioactive colloids are injected into breast cancer or melanoma tumors and absorbed into lymph nodes, a sentinel lymph node, which is the first lymph node to which the colloids moves, can be imaged, dissected, and biopsied to determine whether cancer cells metastasized to the sentinel lymph node. Thus, there is an advantage in that unnecessary dissection of lymph nodes during surgical operations can be avoided. However, the probe having a radioactive isotope conjugated thereto is a probe that is used to determine the position and orientation of lymph nodes before a surgical operation, and has a shortcoming in that it cannot be used for real-time imaging during a surgical operation. Thus, it is required to develop a probe that can be used for real-time imaging during a surgical operation.

Under such technical circumstances, the present inventors have found that a complex of indocyanine green and mannosyl serum albumin overcomes the shortcoming of low in vivo stability of indocyanine green, and that when it is injected during a surgical operation, it can accurately detect the position of lymph nodes by detecting and imaging macrophages abundantly present in lymph nodes, thereby completing the present invention.

DISCLOSURE OF INVENTION

Technical Problem

It is an object of the present invention to provide a complex of mannosyl serum albumin and indocyanine green, which overcomes the shortcoming of low in vivo stability of indocyanine green and can be used as an optical imaging probe for the detection of a sentinel lymph node, a preparation method thereof, and an optical imaging probe comprising the same, and a kit comprising the probe.

Technical Solution

The present invention provides a complex represented by the following formula 1, which comprises indocyanine green conjugated to mannosyl serum albumin:

$$(\text{Man})_m\text{-L-SA-(ICG)}_n \qquad \text{Formula 1}$$

wherein Man is a mannosyl group, L is a linker that may be present or not, SA is serum albumin, ICG is indocyanine green, m is an integer ranging from 1 to 42, and n is an integer ranging from 1 to 34.

The present invention also provides an optical imaging probe for detecting a sentinel lymph node, which comprises the complex.

The present invention also provides a kit comprising the probe.

The present invention also provides a method for preparing the above complex, the method comprising the steps of:
(a) reacting mannose with serum albumin to prepare mannosyl serum albumin; and (b) conjugating indocyanine green to the mannosyl serum albumin prepared in step (a).

Advantageous Effects

The complex according to the present invention can increase the in vivo stability and half-life of indocyanine green, and can detect macrophages in lymph nodes during a surgical operation. Thus, it can be effectively used as an imaging probe for detection of lymph nodes during a surgical operation in the surgical field.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
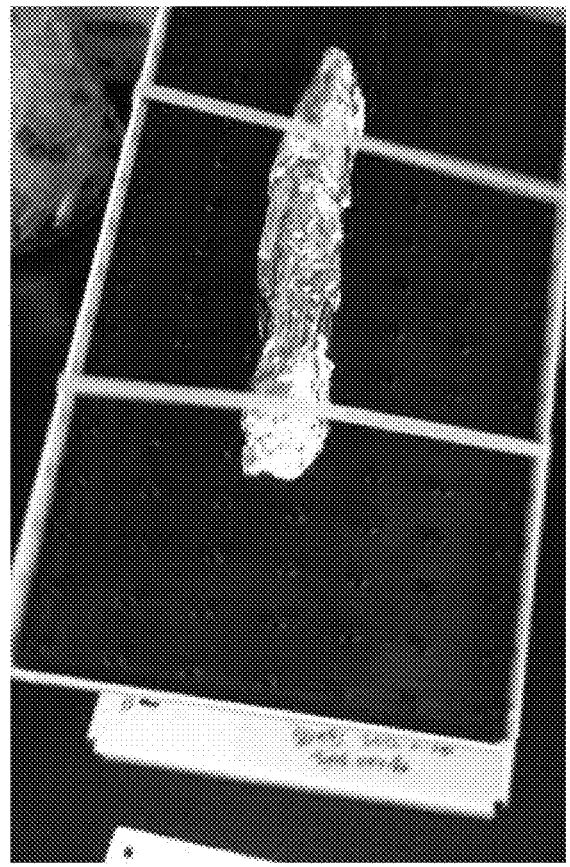
FIG. 1 shows a process for performing a reaction for preparing mannosyl serum albumin (MSA).

In one aspect, the present invention is directed to a complex represented by the following formula 1, which comprises indocyanine green conjugated to mannosyl serum albumin:

(Man)m-L-SA-(ICG)n            Formula 1 wherein Man is a mannosyl group, L is a linker that may be present or not, SA is serum albumin, ICG is indocyanine green, m is an integer ranging from 1 to 42, and n is an integer ranging from 1 to 34.

A complex of indocyanine green and mannosyl serum albumin according to the present invention can overcome the shortcoming of low stability of indocyanine green that can be used for imaging during a surgical operation. Also, it enables imaging that targets macrophages abundantly present in lymph nodes, unlike when indocyanine green conjugated to conventional serum albumin is used. Thus, the complex of the present invention can be effectively used as an imaging probe for detection of lymph nodes during a surgical operation in the surgical field.

The serum albumin (SA in formula 1) that is used in the present invention is a human serum albumin protein having a molecular weight of 66,462, a long axis length of 8 nm, a short axis length of 6 nm, and an isoelectric point (IEP) of 4.8. In addition, it forms 50% (4 g/dl) of serum protein, and consists of single polypeptide chains.

The serum albumin may be in a reduced or unreduced form. Preferably, it may be a reduced form of serum albumin containing thiol groups (—SH). The serum albumin has 17 disulfide bonds, and thus can be reduced using a conventional reducing agent. When it is reduced, 2-34 thiol groups can be produced. The thiol groups can act as functional groups to which indocyanine green can be bonded.

The reduced form of serum albumin containing thiol groups can be stable in the presence of oxygen, and the stability thereof can be increased at a low pH of less than 6. When the reduced form of serum albumin is cooled to the temperature of liquid temperature, it can be stored for a long period of time without contaminating or damaging the thiol groups.

Mannosyl serum albumin is obtained by bonding mannose and serum albumin to each other directly or via a linker. The linker may be, for example, one or more selected from the group consisting of a substituted or unsubstituted $C_1$-$C_{10}$ alkyl group, a substituted or unsubstituted $C_4$-$C_{10}$ aryl group, monopeptides, dipeptides, oligopeptides, a $C_4$-$C_{10}$ cycloalkyl group, a benzyl group, thioether, ether, amine, hydrazide, pentose, hexose, and alcohols. Preferably, the linker may be a phenyl group.

The following structural formula 1 shows a serum albumin conjugated to phenyl mannose using a phenyl group as a linker. It may comprise 1-42 mannoses or linker-containing mannose:

Structural Formula 1

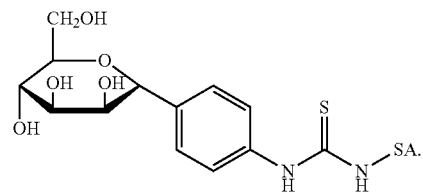

The phenyl mannosyl serum albumin of structural formula 1 can be prepared according to the following reaction scheme 1. For example, a stable phenyl mannosyl serum albumin can be prepared by bonding the amino group of serum albumin to the thiocyano (SCN) moiety at the end of the phenyl group:

Reaction Scheme 1

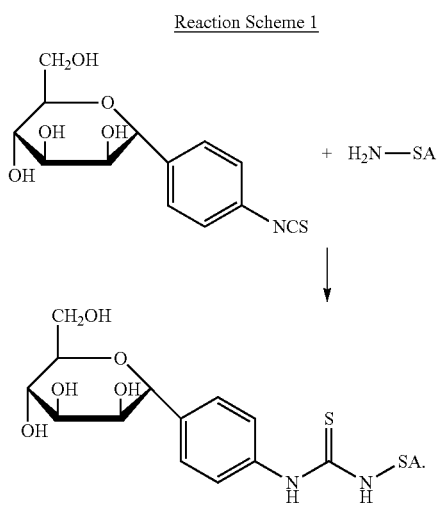

Indocyanine green may, for example, be bonded directly to mannosyl serum albumin or may be bonded to the thiol group. Mannosyl serum albumin bonded to indocyanine green strongly binds to the mannosyl receptor of macrophages and is accumulated in lymph nodes, and thus can be used to image lymph nodes. Particularly, serum albumin has a size of 6-8 nm, which is smaller than that of colloidal radioactive drugs that are currently used, and thus it is rapidly absorbed into lymph nodes.

In some embodiments, the complex may further comprise a metallic radioisotope conjugated thereto, as represented by the following formula 2:

RI-(Man)m-L-SA-(ICG)n        Formula 2 wherein Man is a mannosyl group, L is a linker that may be present or not, SA is serum albumin, ICG is indocyanine green, RI is a metallic radioisotope, m is an integer ranging from 1 to 42, and n is an integer ranging from 1 to 34.

This complex comprising a metallic radioisotope in addition to indocyanine green enables real-time target imaging during a surgical operation by indocyanine green, and can also determine the position and orientation of the target. Thus, it is more effectively used as a probe for imaging the lymphatic system.

Herein, the serum albumin may be a reduced form of mannosyl serum albumin, and may have thiol groups produced by reduction of disulfide bonds (S—S).

Further, the metallic radioisotope may be one or more selected from the group consisting of $^{99m}$Tc, $^{188}$Re, $^{186}$Re, $^{67}$Cu, $^{212}$Pb, $^{212}$Bi and $^{109}$Pd. Preferably, it is $^{99m}$Tc or $^{188}$Re.

In another aspect, the present invention is directed to a method for preparing a complex of mannosyl serum albumin and indocyanine green, the method comprising the steps of: (a) reacting mannose with serum albumin to prepare mannosyl serum albumin; and (b) conjugating indocyanine green to the mannosyl serum albumin prepared in step (a).

In step (a), mannose may be reacted with serum albumin to prepare mannosyl serum albumin. Preferably, IME-thiomannose (2-imino-2-methoxyethyl thiomannose) may be reacted with serum albumin to prepare mannosyl serum albumin.

In some embodiments, a reduced form of mannosyl serum albumin can be prepared by reducing the disulfide bonds of serum albumin with a reducing agent to produce thiol groups. When the disulfide bonds of serum albumin are reduced to thiol groups, serum albumin bonded to phenyl mannose using a phenyl group as a linker may have a structure represented by the following structural formula 2:

Structural Formula 2

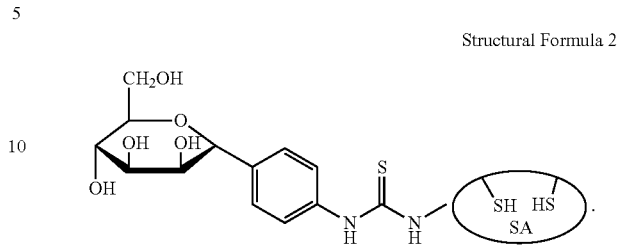

As the reducing agent, a thiol-containing reducing agent is mainly used, such as 2-mercaptoethanol, dithiothreitol, thioglycolate, or cysteine LC glutathione. In addition, thiol-containing reducing agents that are used in the art may also be used. Additionally, a chelating agent may be added to remove residual metal ions to thereby increase the stability of the produced compound.

Specifically, the mannosyl serum albumin having the structure of structural formula 2 is prepared according to the following reaction scheme 2:

Reaction Scheme 2

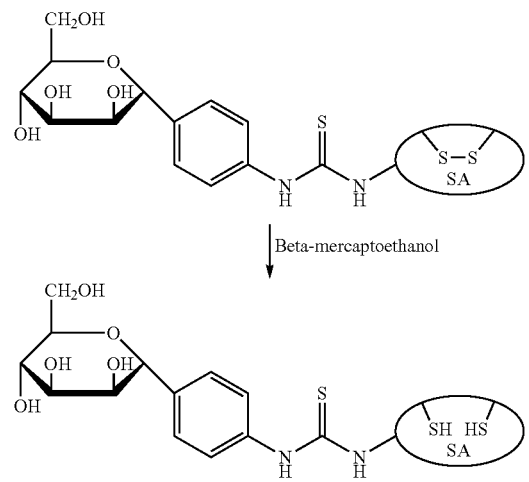

Subsequently, in step (b), indocyanine green is conjugated to the mannosyl serum albumin. In step (b), a complex comprising indocyanine green conjugated to the mannosyl serum albumin can be prepared by reacting the serum albumin with indocyanine green in about 10 mM of phosphate buffer at a molar ratio of 1:1 to 1:15, for example, 1:2 to 1:10, preferably 1:5 to 1:10. When mannosyl serum albumin and indocyanine green are used at a molar ratio within the above range, a stable mannosyl serum albumin-indocyanine green complex can be prepared, and if they are used at a molar ratio out of the above range, indocyanine green having no mannosyl serum albumin conjugated thereto can be obtained, because the conjugation of mannosyl serum albumin is not stable.

In some embodiments, when the complex further comprises a metallic radioisotope, the preparation method according to the present invention may further comprise a step of conjugating a metallic radioisotope to the mannosyl serum albumin conjugated to indocyanine green. For example, the complex further comprising a radioisotope can be prepared by reacting 0.1-500 mCi/mg of a radioisotope with the indocyanine green-conjugated mannosyl serum albumin at room temperature for 0.1-30 minutes.

Herein, the serum albumin may be a reduced form of mannosyl serum albumin, and may have thiol groups produced by reduction of disulfide bonds (S—S). For this, the preparation method according to the present invention may further comprise a step of reducing the disulfide bonds of serum albumin with a reducing agent to produce thiol groups to thereby prepare a disulfide-reduced form of mannosyl serum albumin.

In still another aspect, the present invention is directed to an optical imaging probe for detecting a sentinel lymph node, which comprises the above complex, and a method of detecting a sentinel lymph node using the above complex as an optical imaging probe, the method comprising the steps of:

(a) administering the complex to a subject; and (b) acquiring a fluorescence distribution image of the complex and imaging a tumor.

When this probe is used, cells present in lymph nodes can be accurately detected. In some embodiments, when the complex further comprising a metallic radioisotope conjugated thereto is used as a probe, it is possible to image a target before and during a surgical operation.

The probe according to the present invention shows a high binding affinity and specificity for a sentinel lymph node. As used herein, the term "binding affinity" refers to an affinity on the order of nanomole or higher. The imaging probe according to the present invention shows the optimum biodistribution, metabolism, pharmacokinetics, and elimination properties.

In still another aspect, the present invention is directed to an optical imaging probe for tumor imaging, which comprises the above complex, and a method of imaging a tumor using the above complex as an optical imaging probe, the method comprising the steps of:

(a) administering the complex to a subject; and (b) imaging the tumor by acquiring a fluorescence distribution image of the complex according to the present invention.

As used herein, the term "tumor" is intended to include metastatic or non-metastatic benign tumors and malignant tumors (cancers). Examples of the tumor include, but are not limited to, breast cancer (e.g., invasive ductal carcinoma, ductal carcinoma in situ, inflammatory breast cancer, etc.), renal cancer (e.g., renal cell carcinoma, renal pelvic and ureteral cancer, etc.), ovarian cancer (e.g., epithelial ovarian cancer, extragonadal germ cell tumor, ovarian germ cell tumor, ovarian tumor of low malignant potential, etc.), lung cancer (e.g., non-small-cell lung cancer, small-cell lung cancer, malignant mesothelioma, etc.), prostate cancer (e.g., hormone-dependent prostate cancer, hormone-independent prostate cancer, etc.), pancreatic cancer (e.g., pancreatic ductal cancer, etc.), stomach cancer (e.g., papillary adenocarcinoma, mucinous adenocarcinoma, adenosquamous carcinoma, etc.), colon cancer (e.g., gastrointestinal stromal tumor, etc.), rectal cancer (e.g., gastrointestinal stromal tumor, etc.), colorectal cancer (e.g., familial colorectal cancer, hereditary non-polyposis colorectal cancer, gastrointestinal stromal tumor, etc.), small bowel cancer (e.g., non-Hodgkin lymphoma, gastrointestinal stromal tumor, etc.), liver cancer (e.g., primary liver cancer, extrahepatic bile duct cancer, etc.), and the like.

In step (a) of administering the complex of the present invention to the subject, the complex may be administered at a dose determined based on the kind or progression degree of the tumor, the subject's age or weight, or the like.

After step (a), step (b) of acquiring a fluorescence distribution image of the complex to image the tumor is performed. The fluorescence distribution image can be acquired by irradiating near infrared light (700-1000 nm). Herein, the intensity and time of irradiation of near infrared light can be determined depending on the concentration of the complex used or the position and size of the tumor. In some embodiments, fluorescence distribution image can be acquired by visualizing the fluorescence of near infrared light (800-900 nm) of indocyanine green of the complex.

Imaging the tumor in step (b) may be performed, for example, based on the binding of the mannosyl serum albumin of the complex to macrophages in a tumor microenvironment and the fluorescence of indocyanine green.

As used herein, the term "tumor microenvironment" means a complex milieu composed of tumor cells and the surrounding normal cells, extracellular matrix and body fluids. As described in Experimental Example 3, when the mannosyl serum albumin of the complex targets and binds to macrophages that are the major cause of peritumoral inflammation in a tumor microenvironment, and the indocyanine green of the complex bound to macrophages shows fluorescence, the tumor can be imaged by acquiring a fluorescence distribution image.

In a further aspect, the present invention is directed to a kit comprising the above-described probe.

In some embodiments, the kit may optionally comprise a weak chelating agent, an antioxidant or a substance required for operating the kit.

The weak chelating agent functions to prevent the labeling of the weak binding site of mannosyl serum albumin and the production of colloids, and is one or more selected from the group consisting of phosphonate, glucoheptonate, gluconate, glucarate, tartrate, succinate and citric acid. It is preferably included in the kit of the present invention in an amount of 0.1-500 mg per unit dose.

The antioxidant functions to prevent a polymer from being produced by the oxidation and binding of thiol groups. It is preferably vitamin C or gentisic acid, and is preferably included in the kit of the present invention in an amount of 500 mg or less per unit dose.

The kit may be supplemented with a buffer, a sterile vial, physiological saline, a syringe, a filter, a column and other auxiliary devices in order to prepare an inectable agent to be used by a clinical pathologist or technologist. It is known to those skilled in the art that the kit can be changed and modified depending on patient's needs or dietary regimen and can be changed such that a radioactive isotope can be provided or obtained.

EXAMPLES

Hereinafter, the present invention will be described in further detail with reference to examples. It will be obvious to a person having ordinary skill in the art that these examples are illustrative purposes only and are not to be construed to limit or change the scope of the present invention. Also, those skilled in the art will appreciate that various modifications, additions and substitutions are possible based on this illustration, without departing from the scope and spirit of the invention.

Example 1

Preparation of Mannosyl Serum Albumin (MSA)

Preparation of MSA

The components shown in Tables 1 and 2 below were mixed well, and then stirred overnight as shown in FIG. 1. For light shielding, the mixture was covered with an aluminum foil. 268 mg of human serum albumin (HSA) was dissolved in 25 ml of 0.1M $Na_2CO_3$ buffer (pH 9.5), and 25 mg of a-L-mannopyranosylphenyl isothiocyanate was added thereto. The reaction mixture was continuously stirred in a reactor at room temperature for 20 hours, and then frozen at −70° C.

TABLE 1

Preparation of 50 mL of 0.1M buffer (pH 9.5)

| Components | Contents |
|---|---|
| $Na_2CO_3$ (Pure anhydrous sodium carbonate) | 0.1377 g |
| $NaHCO_3$ (Pure sodium bicarbonate) | 0.3108 g |
| DW | 50 ml |

TABLE 2

| Components | Contents |
|---|---|
| Buffer | 0.1M, 5 ml |
| Serum albumin | (26.9 mg/0.134 mL) × 2 = 0.268 mL |
| Mannose-SCN | 2.5 mg |

Purification of MSA

Figure 2:
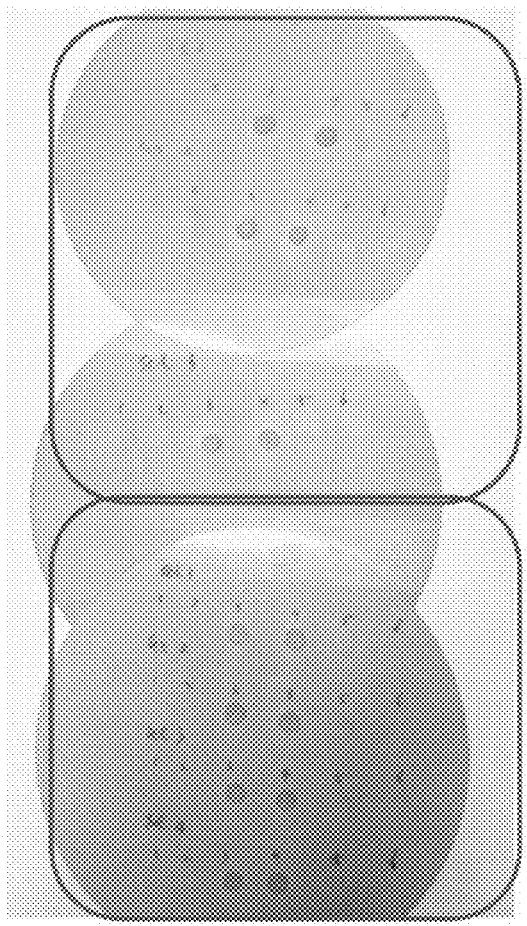
FIG. 2 shows the resulting of staining purified MSA with Coomassie blue to confirm the presence of MSA.
Figure 2:
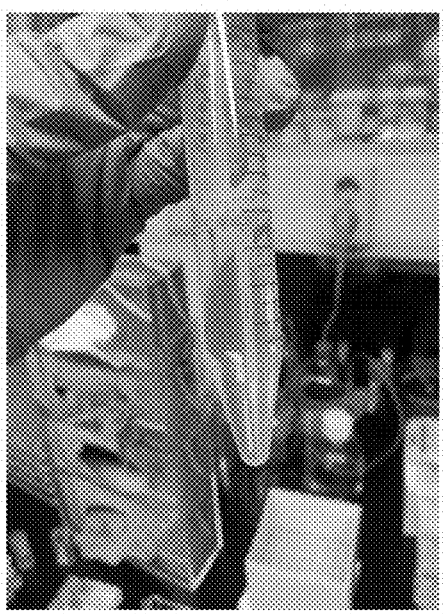

MSA was purified through a PD-10 desalting column using phosphate-buffered saline (pH 6.0) as an eluent. Because the total volume after the reaction for preparation of MSA was 5 mL, which exceeds the loading capacity of the PD-10 column, purification was performed using a total of three column sets (1.5 mL for each column). Before purification, the column was filled with saline, and pre-coated with 1% HAS to prevent MSA from binding nonspecifically to the column. The fractions purified through the column were stained with Coomassie blue to confirm the presence of MSA, and then combined with one another, thereby obtaining a total of 8 mL of MSA solution (FIG. 2). The solution was dispensed into a vial containing 1 mg of protein, and 0.25 mg of sodium medronate, 80 μg of sodium p-aminobenzoate and 13.6 μg of stannous fluoride were added thereto.

Example 2

Quantification of Mannosyl Serum Albumin (MSA)

Analysis of Content

Figure 3:
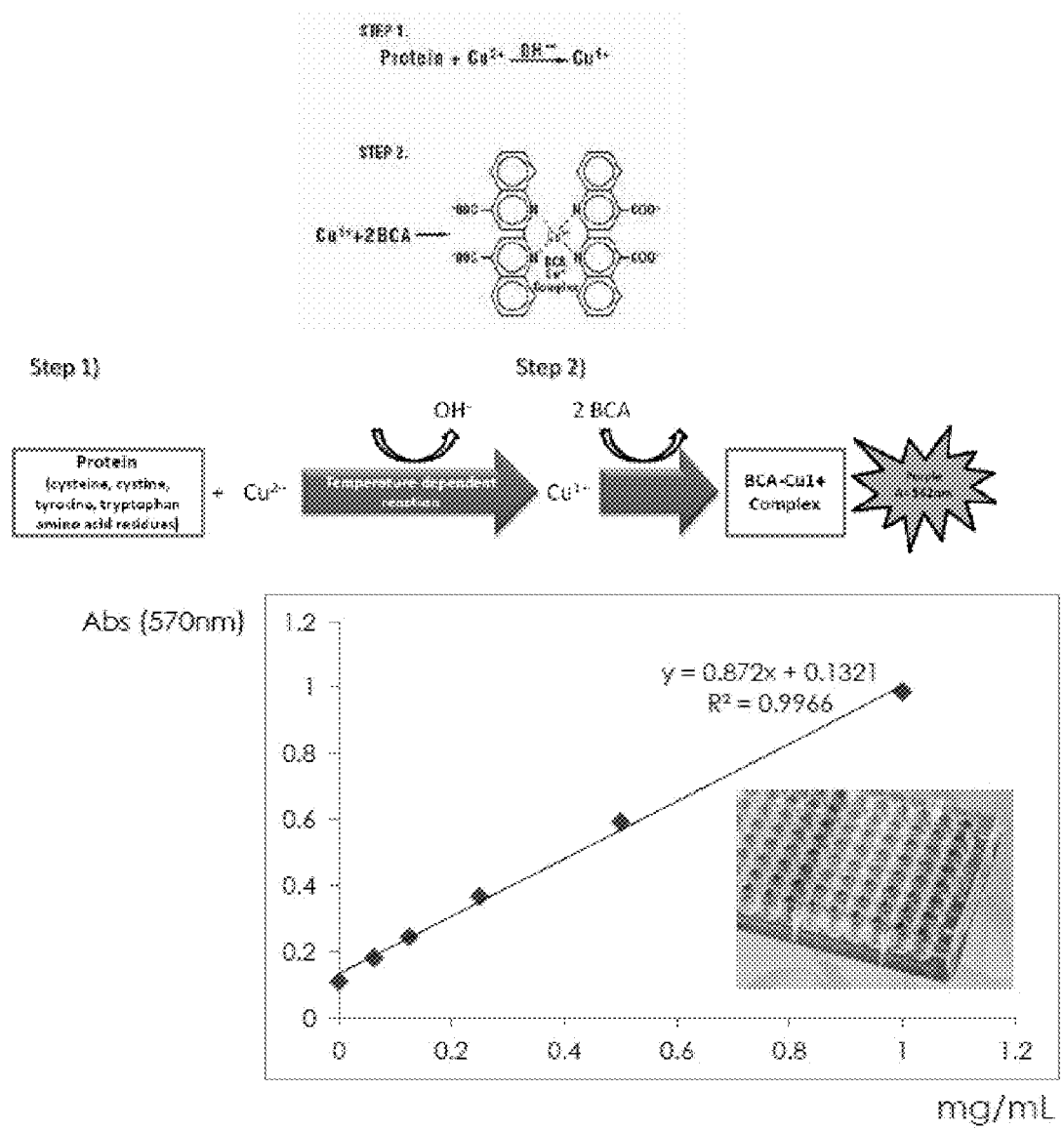
FIG. 3 shows a standard curve used to quantify prepared MSA by a BCA assay.

The MSA obtained in Example 1 was quantified by BCA assay. A standard curve as shown in FIG. 3 was plotted using a standard solution contained in the BCA kit, and the MSA was developed in the BCA kit and measured for absorbance at 570 nm. As a result, it was shown that the MSA of Example 1 was present at a concentration of 2.36 mg/mL.

Measurement of Size

Figure 4:
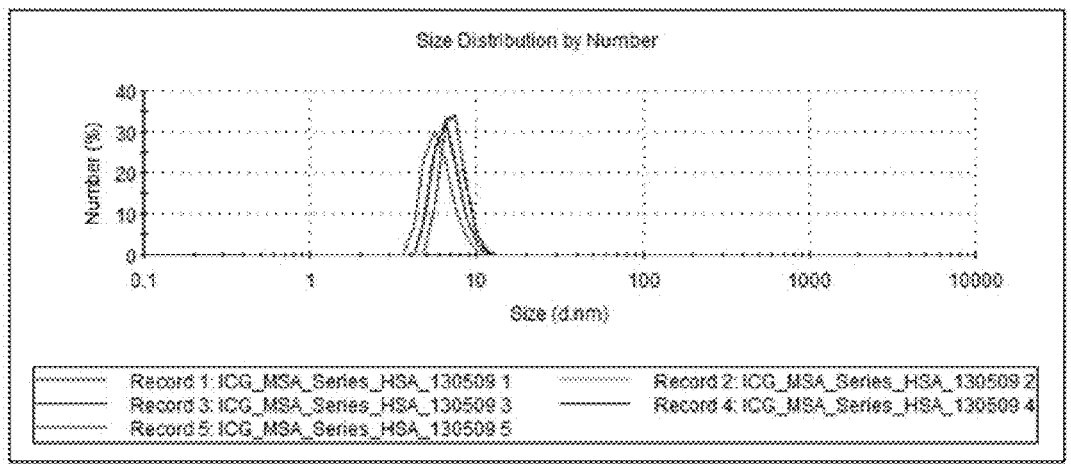
FIG. 4 shows the average size of human serum albumin (HAS), measured by DLS (dynamic light scattering).
Figure 4:
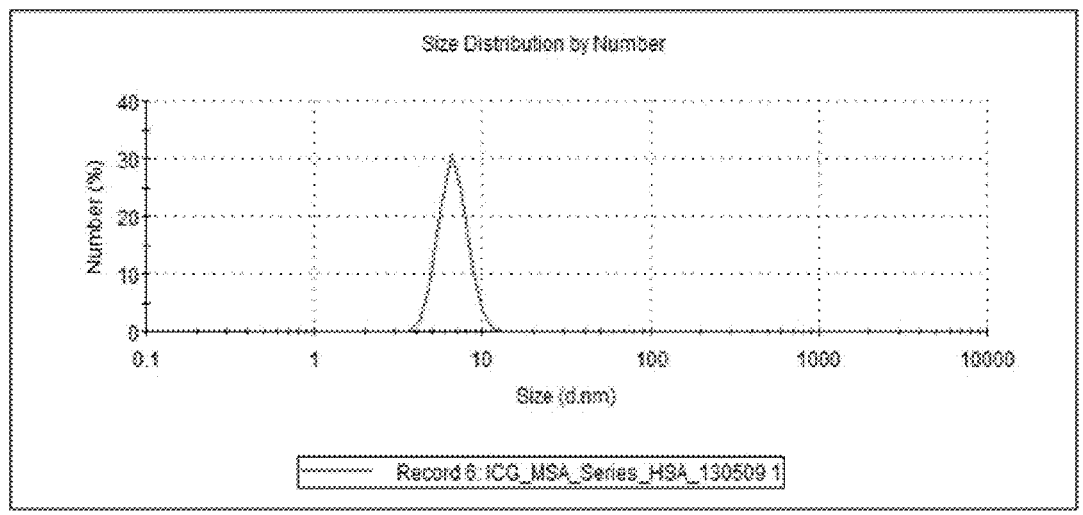
Figure 5:
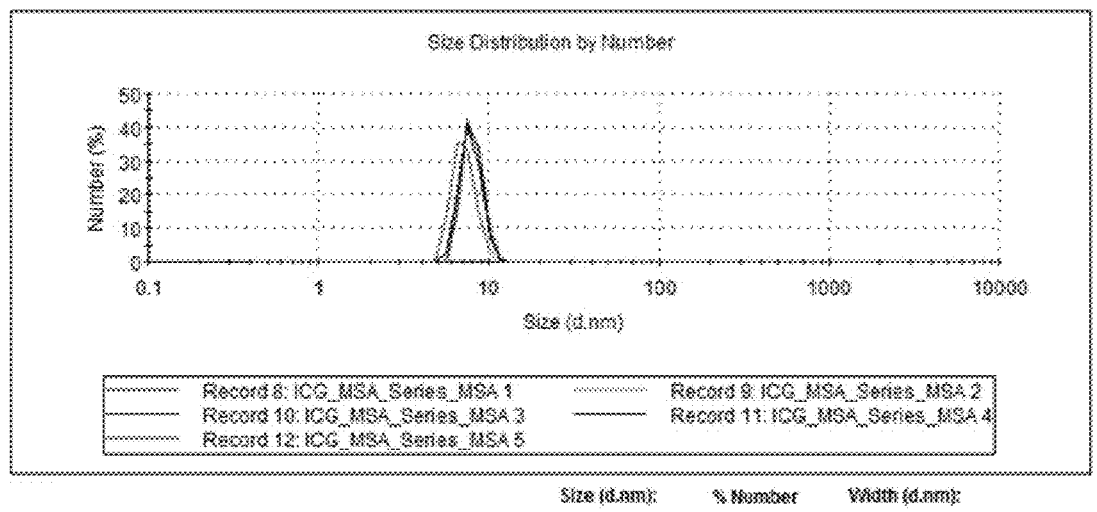
FIG. 5 shows the average size of MSA, measured by DLS (dynamic light scattering).
Figure 5:
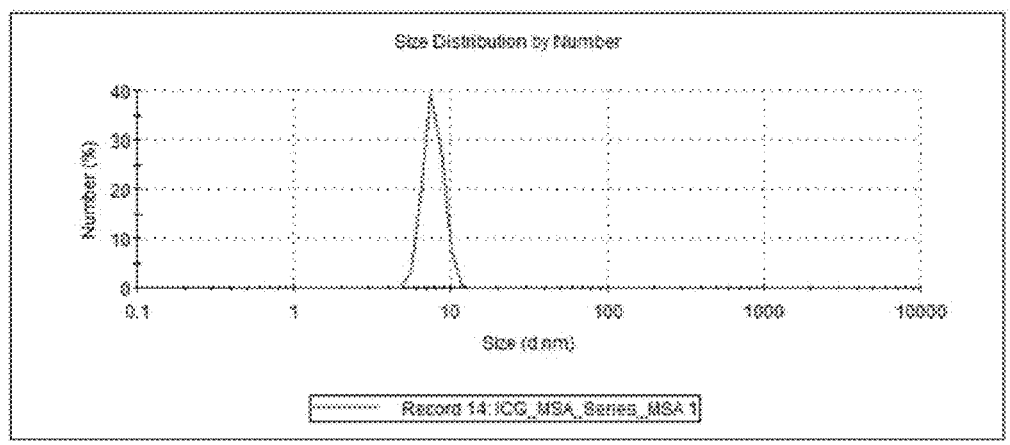

The sizes of HAS and MSA were measured by DLS (dynamic light scattering). The measurement was performed five times in order to ensure uniformity. The results of the measurement indicated that HSA had an average size of 6.80±1.3 nm (FIG. 4) and that MSA had an average size of 7.8±1.1 nm (FIG. 5).

Examination of Physical Properties

The physical properties of MSA were examined. The yield of conjugation between HSA and a-L-mannopyranosylphenyl isothiocyanate was the highest under a weak alkaline condition (pH 9.5). After incubation at room temperature for 20 hours, an ultraviolet assay ($\lambda max=282$ nm) for MSA was performed to measure the number of mannose molecules bound to HAS, and as a result, it was shown that 15.9 mannose molecules were bound per HSA molecule.

Example 3

Preparation of a Complex of Mannosyl Serum Albumin (MSA) and Indocyanine Green (ICG)

MSA synthesized as described in Example 1 was reacted with ICG in 10 mM phosphate buffer (pH=3.1). Herein, MSA and ICG were reacted at molar ratios of 1:1, 1:5, 1:10, 1:15 and 1:20. Because MSA and ICG have molecular weights of about 67 kDa and 774.96 g/mol, respectively, when 1 mg of MSA is used, 0.01156 mg of ICG should be used in order to obtain a molar ratio of 1:1. MSA was used at a concentration of 0.1 mg/12.5 μL (=0.119 mM), and ICG was mixed with MSA at a concentration of 0.001156 mg/0.46 μL for a molar ratio of 1:1, 0.00578 mg/2.3 μL for a molar ratio of 1:5, 0.01156 mg/4.6 μL for a molar ratio of 1:10, 0.01734 mg/6.9 μL for a molar ratio of 1:15, and 0.02312 mg/9.2 μL for a molar ratio of 1:20. To each of the mixtures, 50 μL of 10 mM phosphate buffer (pH=3.1) was added.

Figure 6:
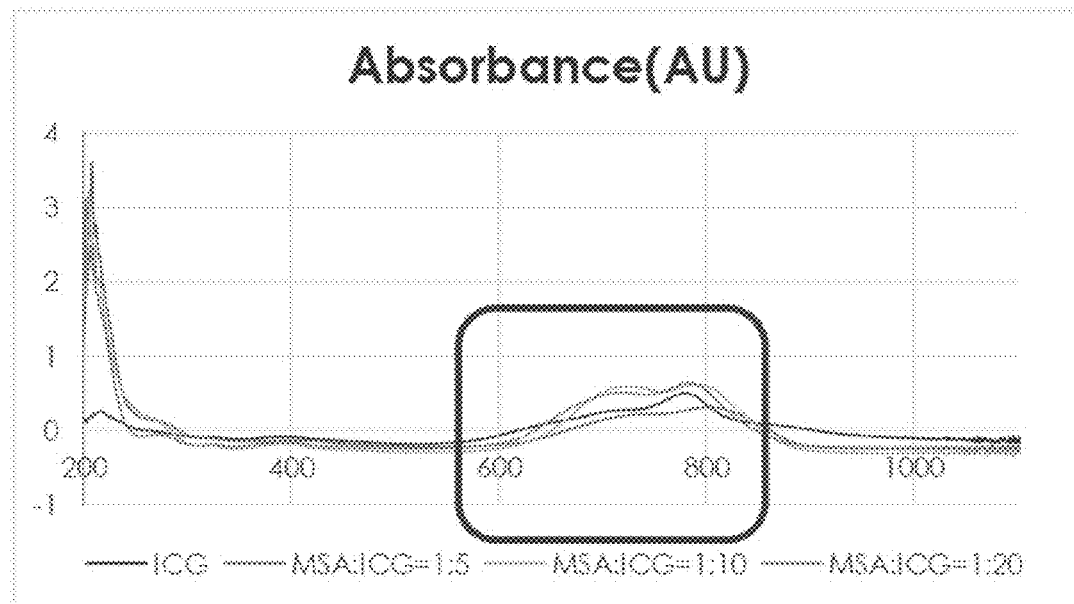
FIG. 6 shows the results of measuring the UV peak of MSA using a UV spectrometer.
Figure 7:
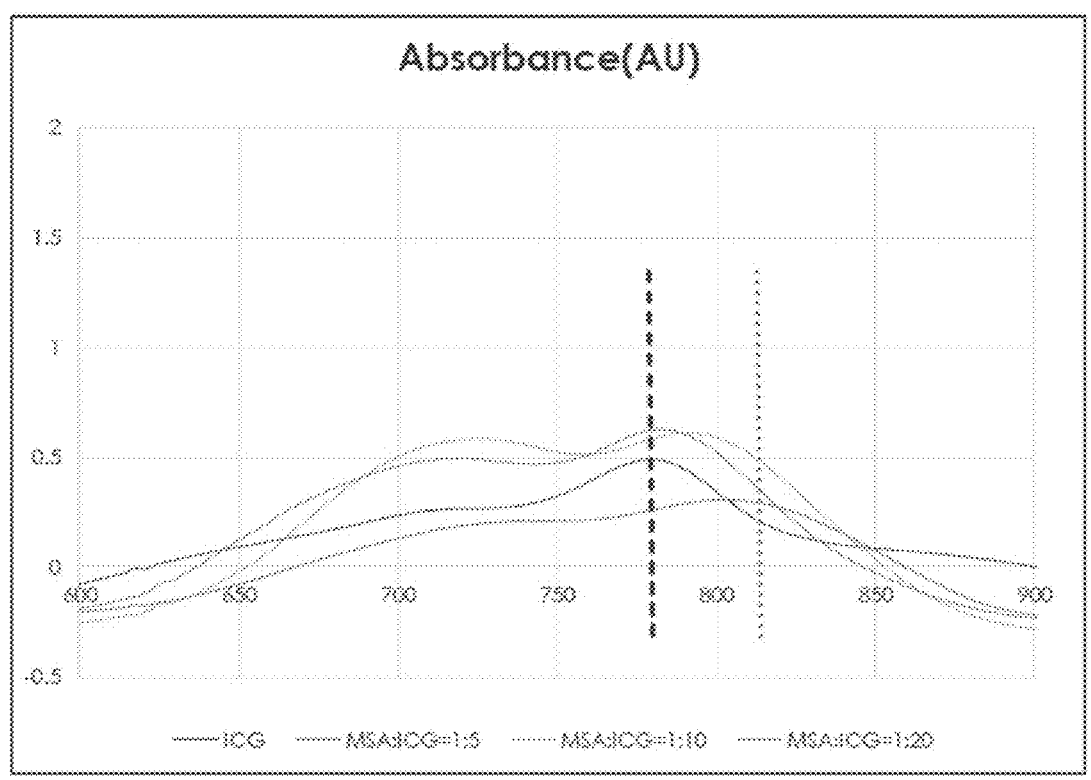
FIG. 7 is an enlarged view of the rectangular portion shown in FIG. 6.

The reaction was monitored by checking the shift of UV peaks using a UV spectrometer. The MSA quantified in Example 2 was reacted with ICG at the indicated molar ratios, and the results of measuring the peaks of the reaction products are shown in FIG. 6. FIG. 7 is an enlarged view of the rectangular portion shown in FIG. 6. Referring to FIGS. 6 and 7, the peak of ICG alone is shown in the first position, and the peak of the MSA/ICG mixture (molar ratio: 1:5) is shown in the second position. It could be seen that, as the ratio of ICG in the mixture increased, the peak approached the original peak of ICG. Also, it was shown that, when MSA and ICG were mixed at a molar ratio of 1:5 to 1:10, an ICG-MSA complex could be prepared.

Example 4

Preparation of $^{99m}$Tc-MSA-ICG Complex

Preparation of a Reduced Form of MSA

To prepare a $^{99m}$Tc-MSA-ICG complex, a step of additionally reducing the MSA prepared in Example 1 should be performed (see Jeong J M, Nuclear Medicine Communications 2004, 25:1211-1217). 10 mg/1 mL of MSA was reacted with a mixture of 40 μL of 0.3M EDTA (ethylenediaminetetraacetic acid) (pH 8.0), 40 μL of 1M sodium bicarbonate and 50 μL of 1.5M β-mercaptoethanol at 37□ for 1 hour. The reduced MSA was purified using a PD-10 column filled with PBS (phosphate buffered saline, pH 6.0).

The purified reduced MSA was dispensed into each vial such that the vial contained 1 mg of protein, 0.25 mg of sodium medronate, 80 μg of sodium p-aminobenzoate and 13.6 μg of stannous fluoride. Each vial was freeze-dried, and then stored in a freezer.

The purified reduced MSA was collected using Ellman's reagent and β-mercaptoethanol, and further purified through a PD10 column. It was shown that the resulting MSA had 19.4 free thiol groups per MSA molecule. Herein, the absorbance was measured at a wavelength of 410 nm, and the standard curve was plotted using a cysteine solution.

Preparation of $^{99m}$Tc-MSA

About 20-30 mCi/mL of $^{99m}$Tc-pertechnetate was added per vial and allowed to react at room temperature for 30 minutes. The reaction product was developed on ITLC-SG (Instant Thin Layer Chromatography-Silica Gel) with ethanol: 10% ammonium acetate=1:1, and measured for labeling efficiency using 5% BSA-impregnated paper developed with saline.

When ITLC-SG was developed with ethanol: 10% ammonium acetate=1:1, $^{99m}$Tc-pertechnetate moved up with the solvent, and MSA-bound $^{99m}$Tc appeared at the origin.

Figure 8:
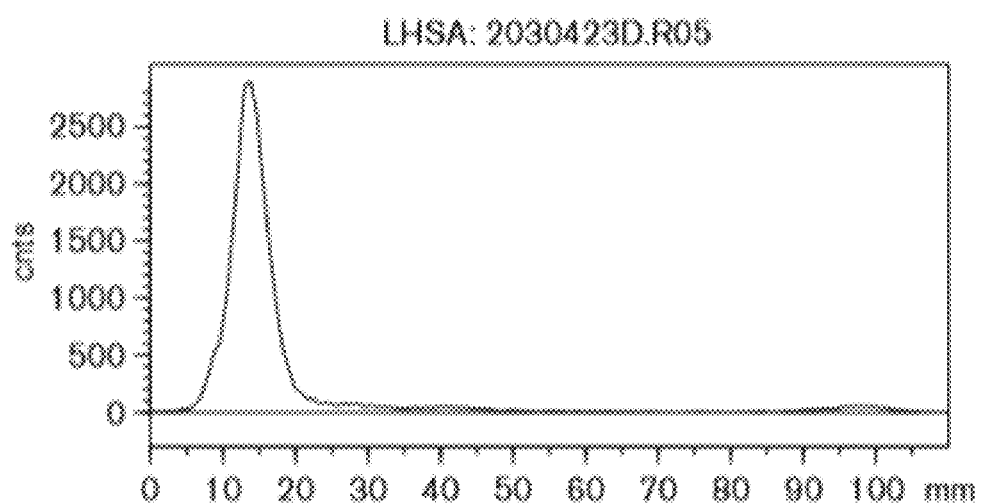
FIG. 8 shows the results of measuring labeling efficiency for prepared $^{99m}$Tc-MSA on ITLC-SG (instant thin layer chromatography-silica gel).

In addition, in 5% BSA-impregnated paper chromatography/saline, it was shown that the labeled MSA appeared at the top with the solvent (FIG. 8).

Mixing with ICG

The shift of UV peaks was observed in the same manner as described in Example 3. In order to prevent the radio-contamination of the instrument, UV peaks should be examined after a sufficient time after labeling. The results of observing the shift of UV peaks indicated that, when the labeled MSA was mixed with ICG at a molar ratio of 1:5 to 1:10, the physical properties thereof did not change compared to ICG:MSA before labeling.

Experimental Example 1

Biodistribution and Imaging of ICG:MSA

Figure 9:
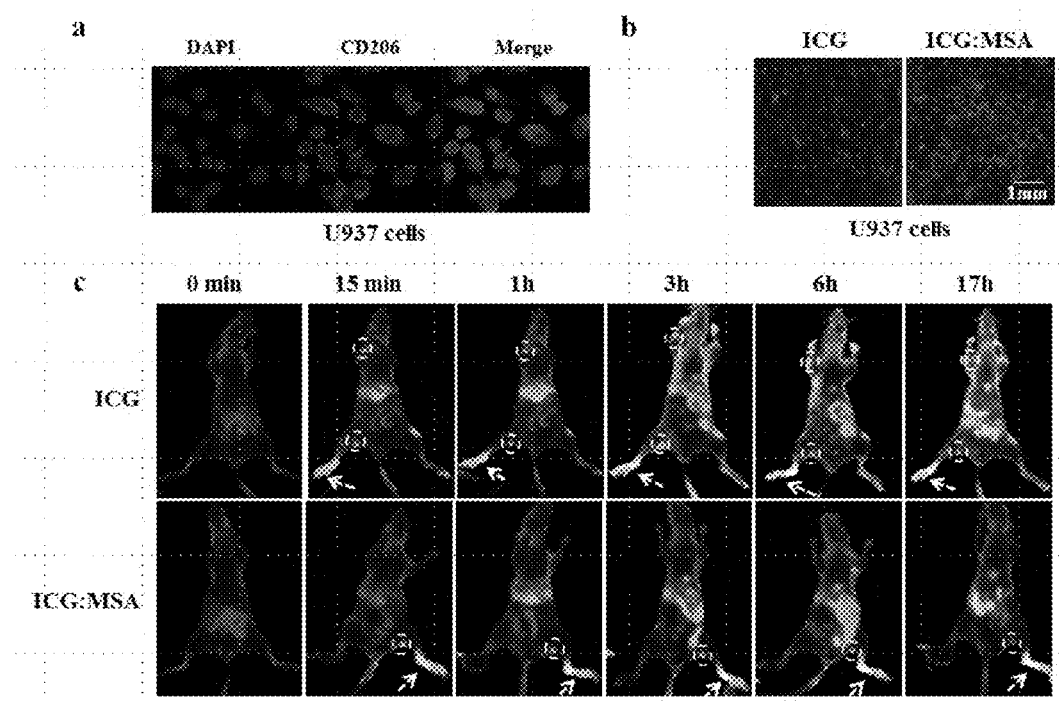
FIG. 9 shows the results of treating activated U937 cells with PMA (Phorbol 12-myristate 13-acetate, Sigma, USA) (FIG. 9a) and activated U937 cells with each of ICG:MSA and ICG (FIG. 9b) and monitoring the distribution of PMA, ICG:MSA and ICG in the cells, with biodistribution after injection of ICG:MSA and ICG in the mouse footpad showing that ICG:MSA was distributed mainly in the lymph nodes (popliteal) and the liver, whereas ICG was distributed in the popliteal lymph nodes and did spread to the axillary lymph nodes within a short time (FIG. 9c).

Each of the ICG: MSA, prepared in Example 3, and ICG, was treated into U937 cells (Korean Cell Line Bank (KCLB) No. 21593.1) activated with PMA (phorbol 12-myristate 13-acetate, Sigma, USA) (FIG. 9a), and the distribution thereof in the cells was monitored. As a result, it was shown that ICG:MSA was much more distributed in the U937 cells (FIG. 9b). In addition, each of ICG:MSA and ICG was injected into the mouse footpad, and the biodistribution thereof was examined. As a result, it was shown that ICG:MSA was distributed mainly in the lymph nodes (popliteal) and the liver, whereas ICG was distributed in the popliteal lymph nodes and did spread to the axillary lymph nodes within a short time (FIG. 9c).

Experimental Example 2

Distribution and Imaging of $^{99m}$Tc-MSA-ICG

The $^{99m}$Tc-MSA prepared in Example 4 was passed through a 0.2 μm syringe filter to obtain a final reaction product. To the reaction product, ICG prepared at a concentration of 10 mg/mL was added and mixed in an amount of 10 μL (MSA:ICG molar ratio=1:10). 10 μL of the prepared $^{99m}$Tc-MSA-ICG was injected into the mouse footpad by a Hamilton syringe. The mice anesthetized with isoflurane were fixed to a SPECT-CT system, and then an image was acquired for 2 minutes. Immediately after imaging at 30 minutes after the injection, a fluorescence image was examined using a Lumina II system. At this time, the image was acquired for 1 second. In addition, the filter was adjusted to an excitation wavelength of 780 nm and an emission wavelength of 845 nm.

Figure 10:
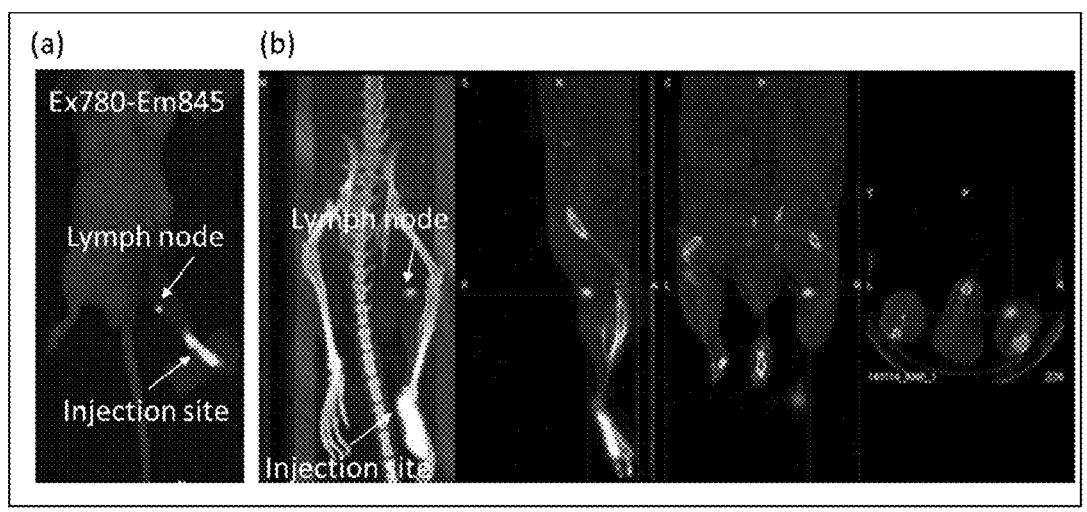
FIG. 10 shows the results of imaging the mouse footpad with a fluorescence imaging system (Lumina II) (FIG. 10a) and SPECT/CT (FIG. 10b) at 30 minutes after injecting $^{99m}$Tc-MSA-ICG into the footpad.

The nuclear medicinal image and fluorescence image obtained as described above are shown in FIG. 10. As can be seen from the images obtained by the fluorescence imaging system (Lumina II) (FIG. 10a) and the SPECT/CT system (FIG. 10b), the lymph nodes appeared at the same position.

Experimental Example 3

Diagnosis by Cancer Imaging using MSA-ICG

The possibility of cancer imaging was examined using the MSA-ICG prepared in Example 3.

(1) ICG vs. ICG:MSA

A VX2 rabbit tumor model (Radiology, 2005; 234:423-430) was established, and after 2 weeks, 60 μM of each of ICG and ICG:MSA was injected subcutaneously into the peritumor of the tumor model. Then, the efficiency with which each of ICG and ICG:MSA detects a sentinel lymph node was examined using a fluorescence imaging system (developed by the applicant).

Figure 11:
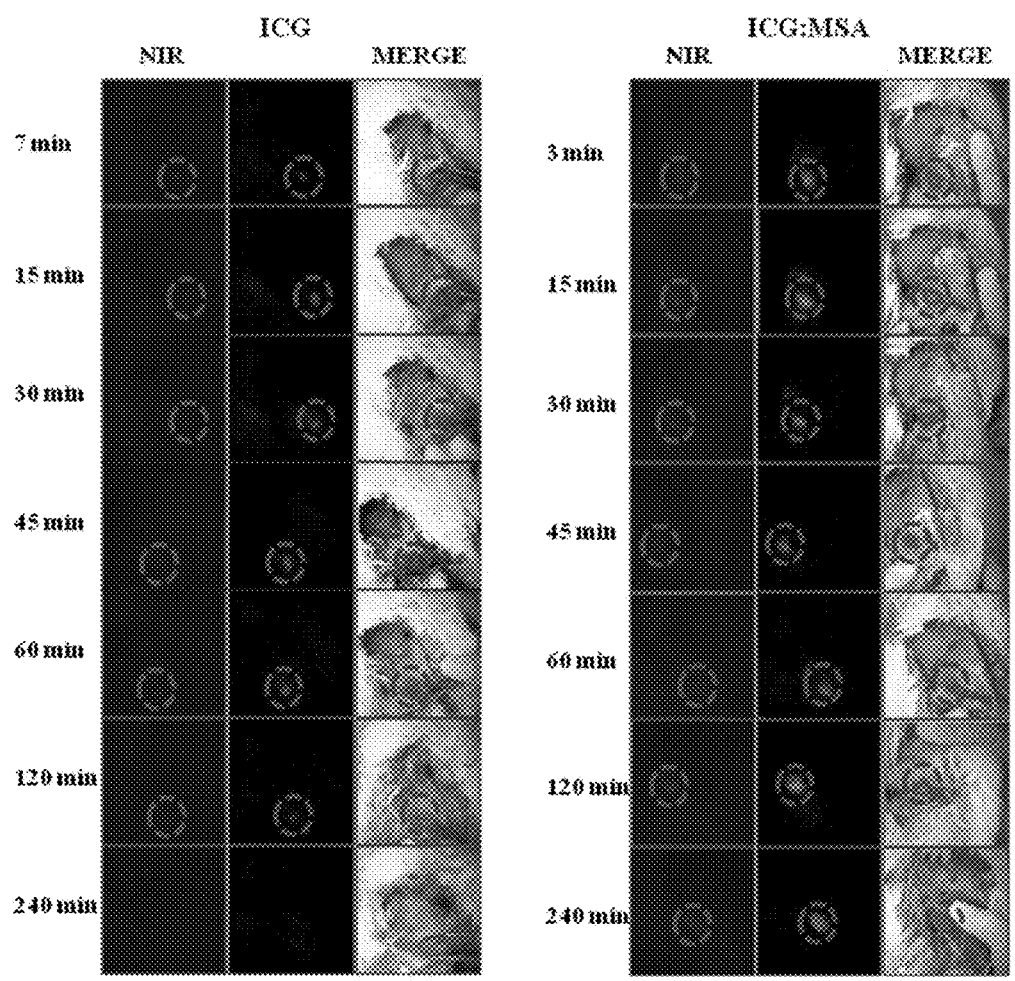
FIG. 11 shows the results of examining the fluorescence signal of ICG:MSA in comparison with that of ICG in sentinel lymph in metastatic sentinel lymph nodes.

The results of the examination are shown in FIG. 11. As can be seen in FIG. 11, the fluorescent signal of the ICG:MSA in the metastatic sentinel lymph node was stronger and longer lasting than the fluorescent signal of ICG. This suggests that MSA binds to macrophages, and it is believed that the reason why the fluorescent signal of the ICG:MSA in the metastatic sentinel lymph node was stronger and longer lasting than the fluorescent signal of ICG alone is because TAMs (tumor associated macrophages) were abundantly present around the tumor.

(2) Detection of Metastatic Sentinel Lymph Node by ICG:MSA

Dissected normal and metastatic lymph nodes were confirmed ex vivo by fluorescence, and whether cancer metastasized to the lymph nodes was examined by H & E tissue staining and immunostaining.

Figure 12:
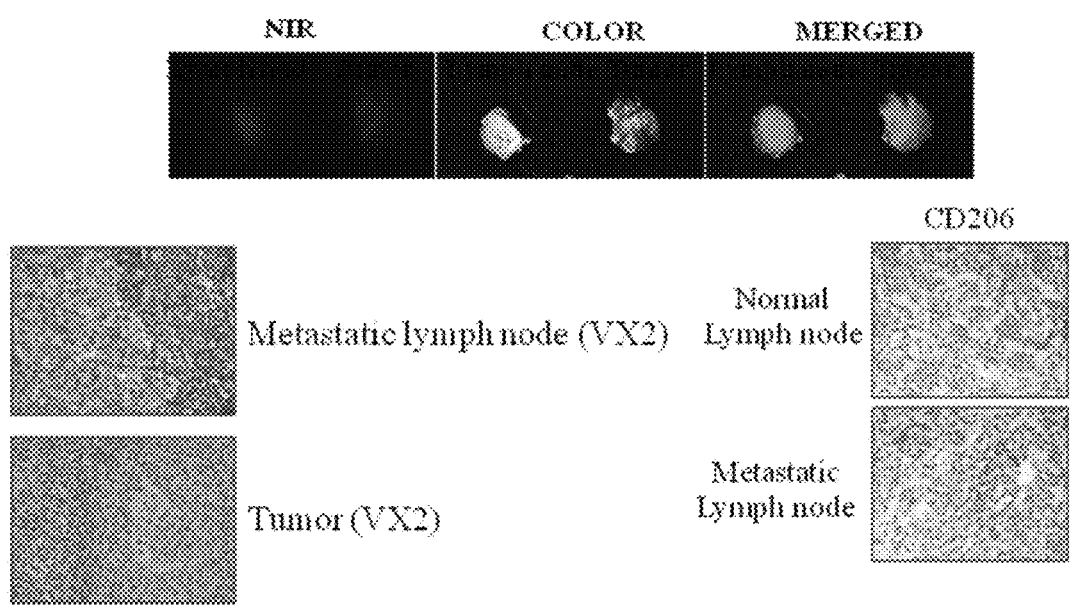
FIG. 12 shows the results of examining whether cancer metastasized to lymph nodes.

The results of the examination are shown in Table 3 below and FIG. 12. As can be seen in Table 3 and FIG. 12, the results of microscopic observation indicated that the tumor metastasized to the lymph nodes, and the expression level of the mannose receptor CD206 was significantly higher in the metastatic lymph node than in the normal lymph node.

TABLE 3

| Group | Total (n = 4) | Metastatic SLN rate | Group | Total (n = 5) | Metastatic SLN rate |
|---|---|---|---|---|---|
| ICG | 2 | 50% | ICG: MSA | 5 | 100% |
| Gamma probe | 3 | 75% | Gamma probe | 5 | 100% |

(3) Examination of Distribution of ICG: MSA in Lymph Nodes

A difference in the distribution of ICG and ICG:MSA in lymph nodes between normal and tumor models was examined.

In order to examine the metastatic lymph node-targeting effect of ICG:MSA, a tumor model mouse (C57BL/6, Orientbio, Seoul, Korea) were established by injecting Lewis lung cancer cells, and ICG:MSA was injected into the footpad of a normal mouse and the tumor model mouse, and then the distribution thereof in the lymph nodes was examined using an fluorescence imaging system (developed by the applicant).

Figure 13:
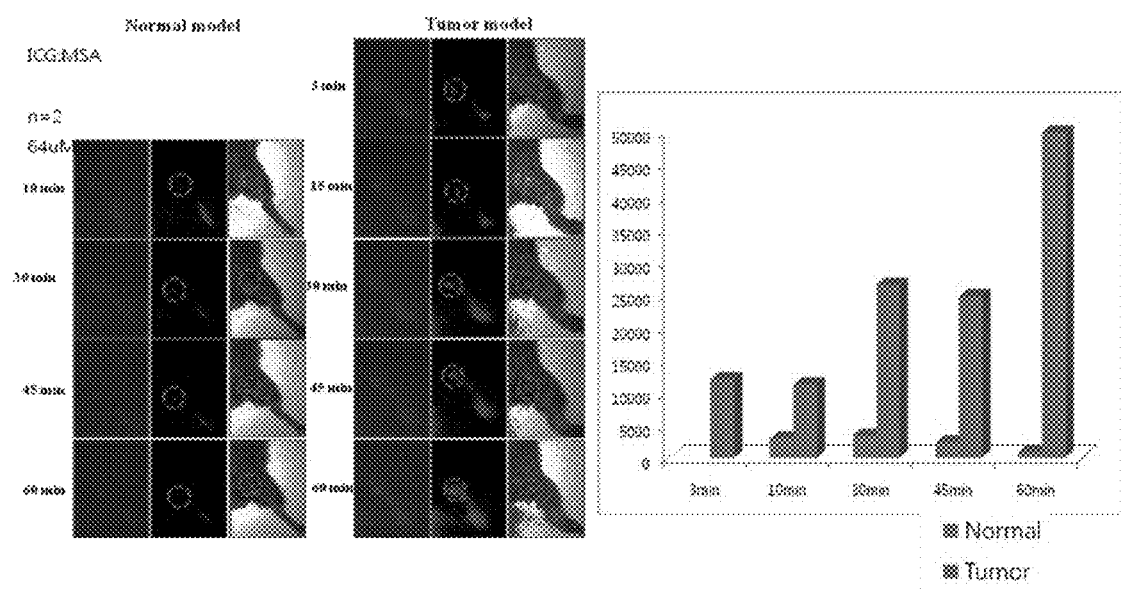
FIG. 13 shows the results of examining the difference in lymph node distribution of ICG and ICG:MSA between a normal model and a tumor model, and shows a graph obtained by quantifying the results.

The results of the examination are shown in FIG. 13. As can be seen in FIG. 13, the ICG:MSA showed a stronger and longer lasting fluorescence in the tumor model, indicating that it is suitable for imaging. The right side of FIG. 13 shows the quantified results, and as can be seen therein, the distribution of the ICG:MSA could be observed from 3 minutes in the tumor model, but could be observed from 10 minutes in the normal model. In addition, it was shown that the distribution of the ICG:MSA in the lymph nodes could be observed up to 1 hour in the tumor model, whereas the fluorescence intensity of the ICG:MSA in the normal model decreased with the passage of time.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of detecting a position of a sentinel lymph node by real-time imaging during a surgical operation, comprising:
   (a) injecting a subject with a complex represented by the following Formula 1

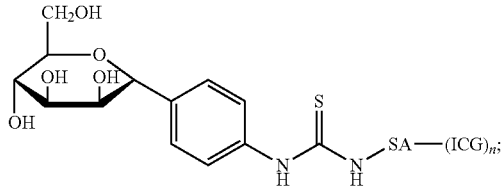

wherein SA is serum albumin, ICG is indocyanine green, and n is 1 to 34, wherein the serum albumin is a reduced form of serum albumin comprising from 2 to 34 thiol groups (—SH), and wherein the indocyanine green is bonded to the thiol groups of the serum albumin; and (b) detecting a position of a sentinel lymph node in the subject by real-time imaging of the complex during a surgical operation.

2. The method of claim 1, wherein step (b) further comprises:
   (i) imaging a fluorescence distribution image of the complex;
   (ii) dissecting fluorescent lymph nodes of the subject; and
   (iii) confirming the presence of tumor metastasized to the sentinel lymph node by staining the sentinel lymph node for cancer cells, to detect a tumor metastasized to the sentinel lymph node.

3. The method of claim 2, wherein the imaging in step (i) is performed to determine whether the mannosyl serum albumin of the complex binds to macrophages in a tumor microenvironment and the indocyanine green produces fluorescence or not.

* * * * *

UNITED STATES PATENT AND TRADEMARK OFFICE
CERTIFICATE OF CORRECTION

PATENT NO. : 10,159,756 B2
APPLICATION NO. : 14/561153
DATED : December 25, 2018
INVENTOR(S) : Hyun Koo Kim et al.

It is certified that error appears in the above-identified patent and that said Letters Patent is hereby corrected as shown below:

On the Title Page

Right hand column, in (74) Attorney, Agent or Firm, the attorney identification of "Steven L. Hultquist" should be -- Steven J. Hultquist --.

Signed and Sealed this
Twenty-ninth Day of January, 2019

Andrei Iancu
*Director of the United States Patent and Trademark Office*